(12) United States Patent
Nakatani et al.

(10) Patent No.: US 6,384,241 B2
(45) Date of Patent: May 7, 2002

(54) PURIFIED SALT OF β-HYDROXYETHOXY ACETIC ACID, PURIFIED 2-P-DIOXANONE, AND MANUFACTURING METHOD THEREFOR

(75) Inventors: Satoru Nakatani; Takuji Matsumoto; Yoshinori Nakahara, all of Wakayama; Hideyuki Akieda, Chiba; Takeshi Ishitoku, Fukuoka, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/820,674

(22) Filed: Mar. 30, 2001

(30) Foreign Application Priority Data

Mar. 21, 2001 (JP) ......................... 2001-079955

(51) Int. Cl.[7] ........................ C07D 407/00; C07C 51/42
(52) U.S. Cl. ........................ 549/274; 562/580; 562/587
(58) Field of Search ........................ 549/274; 562/580, 562/587

*Primary Examiner*—Amelia Owens

(74) *Attorney, Agent, or Firm*—Burns, Doane, Swecker & Mathis, L.L.P.

(57) ABSTRACT

A purified salt of β-hydroxyethoxy acetic acid of formula (1) having a fusion peak-top temperature detected by differential scanning calorimetry (DSC) and a purified 2-p-dioxanone of formula (2) derived from the purified salt of β-hydroxyethoxy acetic acid of formula (1).

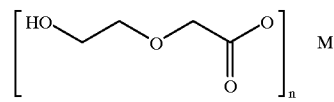

(1)

(wherein in formula (1), n=1–2, and if n=1, M is Na and/or K, and, if n=2, M is Ca and/or Mg.)

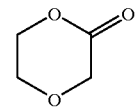

(2)

28 Claims, 2 Drawing Sheets

Fig. 1

PURIFIED SALT OF β-HYDROXYETHOXY ACETIC ACID, PURIFIED 2-P-DIOXANONE, AND MANUFACTURING METHOD THEREFOR

BACKGROUND OF THE INVENTION

1. Field of the Invention

The present invention relates to a purified salt of β-hydroxyethoxy acetic acid, which is a precursor of a purified 2-p-dioxanone.

The present invention relates to a manufacturing method of a purified salt of β-hydroxyethoxy acetic acid, which is a precursor of a purified 2-p-dioxanone.

The present invention relates to a manufacturing method of a purified 2-p-dioxanone obtained from a purified salt of β-hydroxyethoxy acetic acid.

The present invention relates to a method of manufacturing a purified 2-p-dioxanone in an industrially advantageous manner.

The present invention also relates to a purified 2-p-dioxanone having a function to produce a polyparadioxane having a high molecular weight and a narrow molecular weight distribution characterized by not having a carboxyl group at the molecule end, after a polymerization reaction.

The present invention relates to a purified 2-p-dioxanone having a function to produce a polyparadioxane having a high molecular weight and a narrow molecular weight distribution characterized by not detecting a peak in 8.1 ppm attributable to a proton of a carboxyl group by nuclear-magnetic-resonance spectrometry (NMR, measured at 25° C.).

2. Description of the Related Art

[Technical Background of a Salt of β-hydroxyethoxy Acetic Acid]

It has conventionally been said to be a common sense by so-call those skilled in the art that purified salts of β-hydroxyethoxy acetic acid are oily, not crystalline, and that a fusion peak-top temperature is not detected by differential scanning calorimetry (DSC). No literature describes melting points of salts of β-hydroxyethoxy acetic acid.

[Investigation on Salts of β-Hydroxyethoxy acetic acid by the Present Inventors]

The present inventors have thus conducted investigations eagerly and obtained a novel finding that in the course of purification of salts of β-hydroxyethoxy acetic acid, they change from an oily state to crystalline and the fusion peak-top temperature gradually becomes measurable by differential scanning calorimetry (DSC).

According to the novel finding by the present inventors, the fusion peak-top temperature is preferably 205 to 208° C., more preferably 206 to 207° C., further preferably 206.5±0.2° C.

[Technical Background of 2-p-dioxanone]

2-p-Dioxanone is a compound useful as a raw material for a biodegradable and absorbable polymer used in a medicine etc.

[Investigation on 2-p-Dioxanone by the Present Inventors]

In the course of eager investigation on the technology for manufacturing a polydioxane having a narrow molecular weight distribution, the present inventors have obtained a finding that hydrochloric acid and acid chlorides among impurities present in 2-p-dioxanone inhibit manufacturing of a polydioxane having a narrow molecular weight distribution.

In other words, the present inventors have obtained a finding that hydrochloric acid and acid chlorides, if present in 2-p-dioxanone, would generate undesirable impurities due to their high reactivity, and the undesirable impurities involves such a critical problem that even if only a trace amount remains, they promotes ring-opening, cleavage, and degradation of 2-p-dioxanone.

The present inventors have found that if such ring-opening, cleavage, and degradation occur, undesirable impurities having a carboxyl group at ends are produced, which in turns inhibit a ring-opening polymerization reaction, suppress an increase in molecular weight, induce production of undesirable oligomers, and widen a molecular weight distribution as well.

According to the findings of the present inventors as described above, such an empirical rule has been obtained that a molecular weight distribution is wide when a large amount of carboxyl groups are present at molecular ends of a polymer, while a molecular weight distribution is narrow when no carboxyl group is present at molecular ends of a polymer, that is, an amount of carboxyl groups at molecular ends of a polymer is an index of molecular weight distribution.

It is deduced from the above described findings of the present inventors that removal of hydrochloric acid and acid chlorides from 2-p-dioxanone solves the problems of the prior art.

The present inventors have then found that it is quite difficult to remove hydrochloric acid and acid chlorides efficiently from 2-p-dioxanone by purification measures such as distillation and the like.

Then, the present inventors have found that it is quite easy to purify a salt of β-hydroxyethoxy acetic acid, a precursor of 2-p-dioxanone, and reached to consider whether a purified 2-p-dioxanone, which has been purified and requires no further purification, might be readily obtained from a purified precursor, and thus preceded eager investigation.

[Prior Art for Process of Manufacturing 2-p-Dioxanone]

The following prior art can be mentioned with respect to processes of manufacturing 2-p-dioxanone.

(1) Process of Synthesis from 2,3-Dichloro-p-dioxanone

J. Am. Chem. Soc. Vol. 80, 604–608 (1958) discloses a process of manufacturing 2-p-dioxanone in which trans-2,3-dichloro-p-dioxane is reacted with an acid chloride represented by formula (3) to obtain 2-carboxy-3-chloro-p-dioxane (4) represented by the following formula (4), and then 2-carboxy-3-chloro-p-dioxane is subjected to heat treatment to obtain 2,3-dichloro-p-dioxanone.

(3)

(4)

where R represents p-$C_6H_4Cl$, $CH_3$, and H.

This manufacturing process has such a problem that hydrochloric acid and acid chlorides are produced as byproducts, however.

The byproducts, hydrochloric acid and acid chlorides, are highly reactive with an object, 2-p-dioxanone, to produce undesirable impurities. The undesirable impurities involve such a critical problem that even if only a trace amount remains, they promote ring-opening, cleavage, and degradation of 2-p-dioxanone.

When such ring-opening, cleavage, and degradation occur, undesirable impurities having a carboxyl group at ends are produced.

These undesirable impurities in turns inhibit a ring-opening polymerization reaction, suppress an increase in molecular weight, and induce production of undesirable oligomers, and widen a molecular weight distribution as well.

As described above, such an empirical rule has been obtained that a molecular weight distribution is wide when a large amount of carboxyl groups are present at molecular ends of a polymer, while a molecular weight distribution is narrow when no carboxyl group is present at molecular ends of a polymer, that is, an amount of carboxyl groups at molecular ends of a polymer is an index of molecular weight distribution.

In addition, the raw material, 2,3-dichloro-p-dioxanone, also generates hydrochloric acid and acid chlorides as byproducts in its manufacturing process and has problems similar to those described above.

In addition, 2,3-dichloro-p-dioxane, a raw material of this synthetic route, is generally synthesized by a reaction of dioxane with sulfuryl chloride, but each 2 equivalents of HCl and $SO_2$ gases are generated, treatment of which gases is industrially problematic.

(2) Process of Synthesis from Diol Using Catalyst

There have been a great number of reports concerning a method in which diethylene glycol is subjected to a dehydrogenation reaction by heating to a high temperature using a corresponding quantity of a catalyst to obtain 2-p-dioxanone. For example, Japanese Patent Application Laid-Open No. 4-505321 discloses a method of manufacturing 2-p-dioxanone by a catalytic dehydrogenation reaction of dialkylene glycol comprising the step of contacting dialkylene glycol with an effective amount of a dehydrogenation catalyst containing catalytically effective amounts of copper compounds, zinc compounds, and co-catalyst compounds. The selectivity rates in the examples are 73.7 to 99%.

Japanese Patent Application Laid-Open No. 10-120675 describes a process of manufacturing 2-p-dioxanone in which diethylene glycols are contacted with a catalyst comprising copper on a carrier with acid strength (Ho) more than 1.5 and a total amount of acid points in the range of 0 to $2 \times 10^{-7}$ equivalent per square meters in the present of hydrogen at temperature in the range from 200 to 400° C. The selectivity rates in the examples are 95 to 98%.

In addition, in Bull. Chem. Soc., Jpn., vol. 35, 986-(1962), Japanese Patent Application Laid-Open No. 58-99476, U.S. Pat. Nos. 2,807,629, 2,900,395, and 5,391,707, a method to obtain 2-p-dioxanone by a dehydrogenation reaction by heating at a high temperature and using a corresponding amount of a catalyst.

Although selectivity rates have been improved through investigation of catalysts for these manufacturing methods, however, these reactions are still conducted at high temperatures. Thus, in order to treat 2-p-dioxanone that is unstable to heat, a reaction must be conducted in an atmosphere of hydrogen or oxygen and the like so that special high-pressure gas equipments must be employed for manufacturing.

Therefore, special high-pressure gas equipments, considering safety and maintenance and facility management, must be large-scale ones, which is industrially and economically problematic.

(3) Synthesis by Reaction between Diol and Organic Acids

Japanese Patent Application Laid-Open No. 1-299279 describes a manufacturing process in which organic compounds containing at least 2 primary hydroxyl groups in the molecule are subjected to oxidative intramolecular dimerization of the 2 hydroxyl groups using organic acids in the presence of halogen compounds to produce lactone compounds. 2-p-Dioxanone, the object of the present invention, is included in a category of cyclic lactones. The reaction formula of this manufacturing process is shown by formula (5).

(5)

Although this manufacturing process is effective means to obtain lactones, however, carboxylic acid produced in 2 equivalents as a byproduct is highly reactive with 2-p-dioxane and is industrially problematic, considering recovering the product and the like.

(4) Process of Manufacturing from Sodium β-Hydroxyethoxy acetate

Japanese Patent Application Laid-Open No. 60-36785 discloses a process of manufacturing 2-p-dioxanone to be used as a raw material of synthetic absorbable sutures. This process uses inexpensive ethylene glycol and chloroacetic acid as raw materials and can be said an industrial manufacturing process in this respect. The embodiment of this manufacturing process is as follows.

Metal sodium is dissolved in a largely excessive amount of ethylene glycol to obtain glycolate, which is then reacted with choroacetic acid in a quantity of about 0.5 mol per 1 mol of sodium to obtain a sodium salt of hydroxy acid.

After reaction, excess ethylene glycol and reaction byproducts are removed by distillation and washing with acetone, and the sodium salt is converted into a free hydroxy acid by addition of hydrochloric acid. The formed sodium chloride is then removed by sedimentation with ethanol followed by filtration.

After that, a filtrate of the hydroxy acid is slowly heated to about 200° C. preferably in the presence of $MgCO_3$ to remove alcohol and water by distillation. Further heating under atmospheric pressure results in production of p-dioxanone, which is distilled off at a tower top temperature of about 200 to 220° C. It is disclosed that the purity of the crude dioxanone product measured by gas chromatography is generally about 60–70% and its yield is about 50 to 70%.

The crude p-dioxanone is purified by redistillation to a purity of about 98% and finally by multi-step crystallization and/or distillation to a purity not lower than 99%.

(5) Problems of Synthetic Process Described in (4)

The synthetic process of (4) is certainly effective means for synthesis in order to solve the former technical problems.

However, the synthetic process of (4) has such a problem that 2-p-dioxanone obtained at first has a low purity, thus requires several times of purification. That is, considering industrial manufacturing, such complicated operations are problematic in terms of productivity indeed.

The present inventors conducted a follow-up study on the synthetic process (4). The results showed that remaining ethylene glycol as well as remaining glycolates or chloroacetic acid affected the cyclization reaction to reduce the yield. If ethylene glycol remains, it is difficult to separate by distillation due to its boiling point close to that of 2-p-dioxanone, and thus it is difficult to obtain a highly purified 2-p-dioxanone. In addition, 2-p-dioxanone tends to be cleaved by a reaction with the impurity to change to oligomers. If glycolate remains, when hydrochloric acid is added, the sodium salt is detached to produce ethylene glycol and a reaction the same as that described above occurs. If chloroacetic acid remains, it is reactive with the sodium salt of hydroxy acid and 2-p-dioxanone. As a result, production of the byproducts or cleavage of 2-p-dioxanone occurs during the neutralization/cyclization reaction after addition of hydrochloric acid. Although several times of purification is required in order to obtain highly purified and stable 2-p-dioxanone, an actual yield is only about 20 to 30%. This process thus cannot be said an excellent method.

SUMMARY OF THE INVENTION (1) One of the objects of the present invention is to provide a purified 2-p-dioxanone having a function to produce polyparadioxane having a high molecular weight and a narrow molecular weight distribution characterized by not having a carboxyl group at molecular ends after a polymerization reaction.

(2) One of the objects of the present invention is to provide a purified 2-p-dioxanone having a function to produce polyparadioxane having a high molecular weight and a narrow molecular weight distribution characterized in that a peak at 8.1 ppm attributable to a proton of a carboxyl group by nuclear magnetic resonance spectrometry (NMR, measured at 25° C.) is not detected after a polymerization reaction.

(3) One of the objects of the present invention is to provide a purified salt of β-hydroxyethoxy acetic acid, a precursor of a purified 2-p-dioxanone, which can readily be derived to the purified 2-p-dioxanone described in (1) and (2).

(4) One of the objects of the present invention is to provide a process of manufacturing a purified salt of β-hydroxyethoxy acetic acid, a precursor of a purified 2-p-dioxanone, which can readily be derived to the purified 2-p-dioxanone described in (1) and (2).

(5) One of the objects of the present invention is to provide a purified salt of β-hydroxyethoxy acetic acid, a precursor of a purified 2-p-dioxanone, which can readily be derived to the purified 2-p-dioxanone.

(6) One of the objects of the present invention is to provide a process of manufacturing a purified salt of β-hydroxyethoxy acetic acid, a precursor of a purified 2-p-dioxanone, which can readily be derived to the purified 2-p-dioxanone.

(7) One of the objects of the present invention is to provide a process of manufacturing a purified 2-p-dioxanone from a purified salt of β-hydroxyethoxy acetic acid.

(8) One of the objects of the present invention is to provide a process of manufacturing a purified 2-p-dioxanone in an industrially advantageous manner.

(9) One of the objects of the present invention is to provide technology for manufacturing a highly purified 2-p-dioxanone that is suitable as a raw material for polymers having a high molecular weight and narrow molecular weight distribution and contains less impurities at a high yield, considering the problems of the prior art.

(10) One of the objects of the present invention is to provide a purified 2-p-dioxanone, which can produce biodegradable absorbable polymers to be used for drugs and the like and polymers with a high molecular weight and narrow molecular weight distribution that can be extremely suitably used for sutures for surgical operations.

The present inventors considered the problems in the above described "(4) Synthesis from Sodium β-Hydroxyethoxy acetate" in the Prior Art and proceeded research eagerly.

As a result, the present inventors have obtained a novel finding that 2-p-dioxanone is highly reactive with organic acids, especially carboxylic acids or acid halides and substances having a hydroxyl group, especially diols such as ethylene glycol and diethylene glycol and therefore remaining of these substances affects to stability of 2-p-dioxanone, and removal of these impurities largely contributes to remarkable improvement of a reaction yield.

According to the process of manufacturing 2-p-dioxanone of the present invention, after purified sodium β-hydroxyethoxy acetate is first isolated to obtain a precursor (intermediate) containing less impurities, a cyclization reaction is conducted followed by distillation once. As a result, a purified 2-p-dioxanone having a sufficient purity to be used for a monomer can be obtained.

The 2-p-dioxanone obtained by the manufacturing process according to the present invention is a monomer suitable for polymers that have a high molecular weight and a narrow molecular weight distribution required as raw materials of bioabsorbable materials.

The present invention is specified by the items described in [1] to [16] below.

[1] A purified salt of β-hydroxyethoxy acetic acid which is characterized by detecting fusion peak-top temperature by differential scanning calorimetry (DSC) and which is represented by formula (1).

(wherein in formula (1), n=1–2, and if n=1, M is Na and/or K, and, if n=2, M is Ca and/or Mg.)

[2] The purified salt of β-hydroxyethoxy acetic acid as described in [1], characterized in that the fusion peak-top temperature is 205 to 208° C.

[3] The purified salt of β-hydroxyethoxy acetic acid as described in [1], characterized in that the fusion peak-top temperature is 206 to 207° C.

[4] The purified salt of β-hydroxyethoxy acetic acid as described in [1], characterized in that the fusion peak-top temperature is 206.5° C.

[5] A process of manufacturing a purified salt of β-hydroxyethoxy acetic acid represented by the following formula (1), of which a fusion peak-top temperature is detected by differential scanning calorimetry (DSC), characterized in that the process comprises the steps of:
sedimenting a salt of β-hydroxyethoxy acetic acid of formula (1), a fusion peak-top temperature of which is not detected by differential scanning calorimetry (DSC), with a poor solvent; and
washing a sedimented salt of β-hydroxyethoxy acetic acid with the poor solvent, (1)

(wherein in formula (1), n=1–2, and if n=1, M is Na and/or K, and, if n=2, M is Ca and/or Mg.)

[6] The process of manufacturing a purified salt of β-hydroxyethoxy acetic acid as described in [5], characterized in that the fusion peak-top temperature of an obtained purified salt of β-hydroxyethoxy acetic acid is 205 to 208° C.

[7] The process of manufacturing a purified salt of β-hydroxyethoxy acetic acid as described in [5], characterized in that the fusion peak-top temperature of an obtained purified salt of β-hydroxyethoxy acetic acid is 206 to 207° C.

[8] The process of manufacturing a purified salt of β-hydroxyethoxy acetic acid according as described in [5], characterized in that the fusion peak-top temperature of an obtained purified salt of β-hydroxyethoxy acetic acid is 206.5° C.

[9] A purified salt of β-hydroxyethoxy acetic acid represented by the following formula (1) obtained by the production process according to any one of the manufacturing methods described in [5] to [8], (1)

(wherein in formula (1), n=1–2, and if n=1, M is Na and/or K, and, if n=2, M is Ca and/or Mg.)

[10] A process of manufacturing a purified 2-p-dioxanone represented by the following formula (2), characterized in that a purified salt of β-hydroxyethoxy acetic acid represented by the following formula (1), a fusion peak-top temperature of which is detected by differential scanning calorimetry (DSC), is reacted with an inorganic acid, whereby a neutralization reaction and a cyclization reaction are performed in the same system, (1)

(wherein in formula (1), n=1–2, and if n=1, M is Na and/or K, and, if n=2, M is Ca and/or Mg.)

(2)

[11] The process of manufacturing a purified 2-p-dioxanone as described in [10], characterized in that the fusion peak-top temperature of the purified salt of β-hydroxyethoxy acetic acid employed is 205 to 208° C.

[12] The process of manufacturing a purified 2-p-dioxanone as described in [10], characterized in that the fusion peak-top temperature of the purified salt of β-hydroxyethoxy acetic acid employed is 206 to 207° C.

[13] The process of manufacturing a purified 2-p-dioxanone as described in [10], characterized in that the fusion peak-top temperature of the purified salt of β-hydroxyethoxy acetic acid employed is 206.5° C.

[14] A purified 2-p-dioxanone obtained by the manufacturing process described in any one of [10] to

[15] The purified 2-p-dioxanone as described in [14], characterized in that the purified 2-p-dioxanone has a function to produce a polyparadioxane not having a carboxyl group at molecular ends after a polymerization reaction.

[16] The purified 2-p-dioxanone as described in [14], characterized in that the purified 2-p-dioxanone has a function to produce a polyparadioxane for which a peak at 8.1 ppm attributable to a proton of a carboxyl group by nuclear magnetic resonance spectrometry (NMR, measured at 25° C.) is not detected after a polymerization reaction.

The advantages of the present invention are as follows:

(1) One of the advantages of the present invention is to provide a purified 2-p-dioxanone having a function to produce polyparadioxane having a high molecular weight and a narrow molecular weight distribution characterized by not having carboxyl group at molecular ends after a polymerization reaction.

(2) One of the advantages of the present invention is provide a purified 2-p-dioxanone having a function to produce polyparadioxane having a high molecular weight and a narrow molecular weight distribution characterized in that a peak at 8.1 ppm attributable to a proton of a carboxyl group by nuclear magnetic resonance spectrometry (NMR, measured at 25° C.) is not detected after a polymerization reaction.

(3) One of the advantages of the present invention is to provide a purified salt of β-hydroxyethoxy acetic acid, a precursor of a purified 2-p-dioxanone, which can readily be derived to the purified 2-p-dioxanone described in (1) and (2).

(4) One of the advantages of the present invention is to provide a process of manufacturing a purified salt of β-hydroxyethoxy acetic acid, a precursor of a purified 2-p-dioxanone, which can readily be derived to the purified 2-p-dioxanone described in (1) and (2).

(5) One of the advantages of the present invention is to provide a purified salt of β-hydroxyethoxy acetic acid, a precursor of a purified 2-p-dioxanone, which can readily be derived to the purified 2-p-dioxanone.

(6) One of the advantages of the present invention is to provide a process of manufacturing a purified salt of β-hydroxyethoxy acetic acid, a precursor of a purified 2-p-dioxanone, which can readily be derived to the purified 2-p-dioxanone.

(7) One of the advantages of the present invention is to provide a process of manufacturing a purified 2-p-dioxanone from a purified salt of β-hydroxyethoxy acetic acid.

(8) One of the advantages of the present invention is to provide a process of manufacturing a purified 2-p-dioxanone in an industrially advantageous manner.

(9) One of the advantages of the present invention is to provide technology for manufacturing a highly purified 2-p-dioxanone that is suitable as a raw material for polymers having a high molecular weight and narrow molecular weight distribution and contains less impurities at a high yield, considering the advantages of the prior art.

(10) One of the advantages of the present invention is to provide a purified 2-p-dioxanone, which can produce biodegradable absorbable polymers to be used for drugs and the like and polymers with a high molecular weight and narrow molecular weight distribution that can be extremely suitably used for sutures for surgical operations.

DETAILED DESCRIPTION OF THE PREFERRED EMBODIMENTS

Embodiments of the present invention will be described below in detail.

[Investigation on 2-p-Dioxanone by the Present Inventors]

In the course of eager investigation on the technology for manufacturing a polydioxane having a narrow molecular weight distribution, the present inventors have obtained a finding that hydrochloric acid and acid chlorides among impurities present in 2-p-dioxanone inhibit manufacturing of a polydioxane having a narrow molecular weight distribution.

In other words, the present inventors have obtained findings that hydrochloric acid and acid chlorides present in 2-p-dioxanone would generate undesirable impurities due to their high reactivity, and the undesirable impurities involves such a critical problem that even if only a trace amount remains, they promote ring-opening, cleavage, and degradation of 2-p-dioxanone.

The present inventors have found that if such ring-opening, cleavage, and degradation occur, undesirable impurities having a carboxyl group at ends are produced, which in turns inhibit a ring-opening polymerization reaction, suppress an increase in molecular weight, induce production of undesirable oligomers, and widen a molecular weight distribution as well.

According to the findings of the present inventors as described above, such an empirical rule that a molecular weight distribution is wide when a large amount of carboxyl groups are present at molecular ends of a polymer, while a molecular weight distribution is narrow when no carboxyl group is present at molecular ends of a polymer was obtained, that is, an amount of carboxyl groups at molecular ends of polymer is an index of molecular weight distribution.

It is deduced from the above-described findings of the present inventors that removal of hydrochloric acid and acid chlorides from 2-p-dioxanone solves the problems of the prior art.

The present inventors have therefore found that it is quite difficult to remove hydrochloric acid and acid chlorides efficiently from 2-p-dioxanone by purification measures such as evaporation and the like.

Then, the present inventors have found that it is quite easy to purify a salt of β-hydroxyethoxy acetic acid, a precursor of 2-p-dioxanone and reached to consider whether a purified 2-p-dioxanone, which has been purified and required no further purification, might be purified readily obtained from a purified precursor, and thus proceeded eager investigation.

[Compounds represented by Formula (1)]

According to the present invention, salts of β-hydroxyethoxy acetic acid represented by formula (1) can be used as a starting material. In formula (1), n represents 1 to 2, M is Na and/or K when n is 1 and Ca and/or Mg when n is 2. Na, K, Ca, Mg salts and the like can be mentioned as salts, and Na salt is industrially advantageous.

[Isolation of Compounds of Formula (1)]

The salts of β-hydroxyethoxy acetic acid represented by formula (1) are generally synthesized by a reaction of a monosalt of ethylene glycol and a monochloroacetic acid or monochloroacetic acid salt in an ethylene glycol solvent.

The monosalt of ethylene glycol can be readily obtained by a known method in which a largely excessive quantity of ethylene glycol is mixed with an oxide or hydroxide of alkaline metals or alkaline earth metals and a dehydration promoting solvent such as xylene and the like is added to form a salt.

In the present invention, it is useful to use monochloroacetic acid or its salt in a theoretical equivalent quantity in the above described synthetic reaction. When monochloroacetic acid is used, it is useful to use in a molar ratio of preferably 0.4 to 0.5, more preferably 0.47 to 0.49. When a monochloroacetic acid salt is used, it is useful to use in a molar ratio of preferably 0.8 to 1.0, more preferably 0.95 to 0.98.

In the present invention, a poor solvent is charged into the reaction solution to make a salt of β-hydroxyethoxy acetic acid to be slurry crystals, which are isolated by filtration. When a poor solvent used has a higher boiling point than that of a reaction solvent, the reaction solvent may be first distilled off to form slurry crystals, which may be isolated by filtration. This operation may provide crude salts of β-hydroxyethoxy acetic acid as crystals.

As the poor solvents used, for example, hydrocarbons such as benzene, toluene, xylene, cyclohexane, hexane, and heptane; ketones such as acetone, methyl ethyl ketone, and cyclohexanone; alcohols such as methanol and ethanol; and heterocycles such as dioxane and sulfolan can be used alone or in combination.

[Purification of Compounds of Formula (1)]

According to the present invention, crude salts of β-hydroxyethoxy acetic acid obtained in the above are resedimented or suspended with heat to remove impurities, especially monosalts of ethylene glycol and ethylene glycol.

Good solvents used for dissolution at the time of resedimentation, for example, water is used alone, or in combination with alcohols such as methanol and ethanol; and ketones such as acetone, methylethyl ketone, and cyclohexanone. Desirably, it is industrially useful to use water alone.

A temperature for dissolution is preferably 0 to 150° C., more preferably 50 to 100° C.

As poor solvents for resedimentation, for example, hydrocarbons such as benzene, toluene, xylene, cyclohexane, hexane, and heptane; ketones such as acetone, methylethyl ketone, and cyclohexanone; alcohols such as methanol and ethanol; and heterocycles such as dioxane and sulfolan can be used alone or in combination.

As solvents used in thermal suspension, for example, water is used alone, or in combination with hydrocarbons such as benzene, toluene, xylene, cyclohexane, hexane, and heptane; ketones such as acetone, methylethyl ketone, and cyclohexanone; alcohols such as methanol and ethanol; and heterocycles such as dioxane and sulfolan. Resedimentation or thermal suspension may provide highly purified salts of β-hydroxyethoxy acetic acid.

After thermal suspension, in order to crystallize the partly dissolved salts of β-hydroxyethoxy acetic acid, crystals can be taken out from a filtration mother liquid using the above described solvents used for resedimentation to further improve a total yield.

[Synthesis of Compounds of Formula (2)]

The salts of β-hydroxyethoxy acetic acid of formula (1) obtained as described above can be reacted with inorganic acids to perform a neutralization reaction and a cyclization reaction in one pot to obtain 2-p-dioscanone represented by formula (2).

As inorganic acids, for example, halogenated hydrogen, sulfuric acid, phosphoric acid and the like are used. It is useful to use in a theoretical equivalent or less and preferably use in 0.9 to 1.0 equivalent.

This reaction can be conducted without solvent, but it is advantageous to perform using an appropriate quantity of a solvent.

As solvents to be used, for example, hydrocarbons such as benzene, toluene, xylene, cyclohexane, hexane, and heptane; ketones such as acetone, methylethyl ketone, and cyclohexanone; alcohols such as methanol and ethanol; and heterocycles such as dioxane and sulfolan, and water can be mentioned, and they can be used alone or in combination.

In the present invention, a cyclization reaction occurs almost simultaneously with a neutralization reaction between the salts of β-hydroxyethoxy acetic acid represented by formula (1) obtained as described above and the inorganic acids. A reaction temperature at this point in time is preferably from −20 to 150° C., more preferably from −20 to 40° C.

After reaction, the reaction solvent and produced water are removed by distillation under a reduced pressure or ambient pressure, and the produced salt (for example, sodium chloride, sodium sulfate) is removed by filtration under a reduced pressure and the like. After that, 2-p-dioxanone, the object, is obtained by distillation under a reduced or ambient pressure under $N_2$-gas flow.

In the present invention, the salts of β-hydroxyethoxy acetic acid represented by formula (1) obtained by the above described method are reacted with inorganic acids under a relatively mild temperature condition so that a neutralization reaction and a cyclization reaction are conducted in one pot to obtain 2-p-dioxanone represented by formula (2). The 2-p-dioxanone thus obtained is highly pure and does not require further purification.

The embodiments of the present invention will be further illustrated by the following examples.

EXAMPLE 1

(Isolation and Purification of Sodium β-hydroxyethoxy Acetate)

(1) Synthesis of Monosodium Salt of Ethylene Glycol 1,200 g of xylene, 409.7 g (6.60 mol) of ethylene glycol, and 240.0 g (6.00 mol) of sodium hydroxide were mixed with stirring at 130 to 140° C. to perform azeotropic distillation for 21 hours. After cooling to 25° C., a monosodium salt of ethylene glycol was obtained by filtration under a reduced pressure. The yield was 494.2 g and the yield based on sodium hydroxide was 98.5%.

(2) Synthesis of Sodium β-Hydroxyethoxy acetate

To 650 g of ethylene glycol, 210.2 g (2.50 mol) of the monosodium salt of ethylene glycol obtained by the operation described above in (1) was added with stirring and dissolved at 70 to 80° C. Then, 285.5 g (2.45 mol) of sodium monochloroacetate was charged over 1 hour at the same temperature and then stirred at the same temperature for 2 hours to obtain 1145.0 g of sodium β-hydroxyethoxy acetate solution in ethylene glycol.

(3) Isolation and Purification of Sodium β-Hydroxyethoxy acetate

To 1000.0 g of the sodium β-hydroxyethoxy acetate solution in ethylene glycol obtained by the operation described above in (2), 920 g of sulfolan was added and then ethylene glycol was distilled off under a reduced pressure at 110° C. After cooling to 25° C., filtration under a reduced pressure, washing with 100 g of sulfolan, and washing with 100 g of acetone, and dry with warm air at 65° C. were conducted to obtain 441.5 g of sodium β-hydroxyethoxy acetate. The content of sodium β-hydroxyethoxy acetate was 69.7%, and the contents of other substances were 29.5% for sodium chloride, 0.5% for monosodium salt of ethylene glycol, and 0.3% for ethylene glycol. The yield based on sodium monochloroacetate was 96.9%.

Then, 300 ml of ion exchange water and 1,000 ml of methanol were added and suspended with stirring at 70° C. for 20 minutes. After cooling to 50° C., 1,800 ml of acetone was added to precipitate crystals that were partly dissolved. After filtration and dry, 391.8 g of crystals were obtained. The content of sodium β-hydroxyethoxy acetate was 70.7% and the contents of other substances were 29.2% for sodium chloride, and 0% for monosodium salt of ethylene glycol and ethylene glycol. The yield based on sodium monochloroaceate was 82.0%.

The results of nuclear magnetic resonance spectrometry were as follows: $^1$H-NMR (400 MHz, $D_2O$, δ ppm), 3.944 (s, 2H), 3.719 (m, 2H), 3.623 (m, 2H); $^{13}$C-NMR (100 MHz, $D_2O$, δ ppm), 61.060, 70.397, 72.342.

The melting point of this purified sodium β-hydroxyethoxy acetate was 206.5° C.

Figure 1:
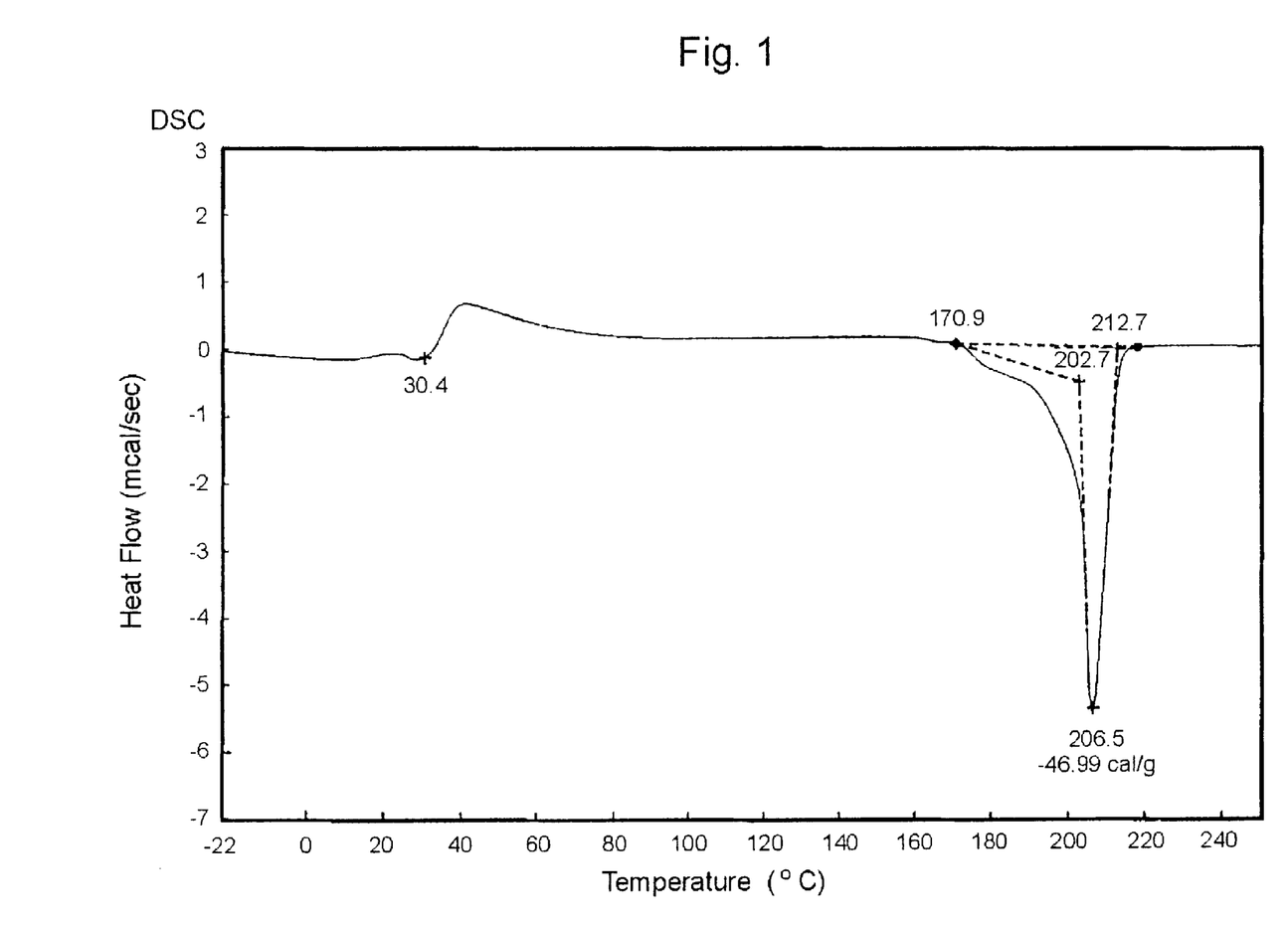
FIG. 1 shows the results of differential scanning calorimetry (DSC) for the purified salt of β-hydroxyethoxy acetic acid (purified sodium β-hydroxyethoxy acetate obtained in Example 1) according to the present invention.

FIG. 1 shows the results of differential scanning calorimetry (DSC) for the purified salt of β-hydroxyethoxy acetic acid (purified sodium β-hydroxyethoxy acetate obtained in Example 1) according to the present invention.

The differential scanning calorimetry (DSC) chart shows that a fusion peak-top is detected at 206.5° C.

Known and publicly used salt of β-hydroxyethoxy acetic acid (sodium β-hydroxyethoxy acetate) is oily and such a peak-top cannot be detected for it.

The measurement conditions for differential scanning calorimetry (DSC) are as follows: About 6.8 to 7.0 mg of a sample was weighed into an aluminum pan. The first temperature was set at −67° C. and DSC measurement was conducted with increasing temperature from −40° C. to 260° C. at a rate of 5° C./min. The used measurement apparatus was RIGAKU DSC 8230 and the standard substance was aluminum oxide.

The abscissa axis shows a scanning range for temperature, and the ordinate axis shows exothermic/exothermic calorie.

EXAMPLE 2

(Synthesis of 2-p-Dioxanone)

301.5 g (1.50 mol) of sodium β-hydroxyethoxy acetate obtained by the method of Example 1 was mixed with 500 ml of methanol, to which 151.0 g (1.45 mol) of 35% hydrochloric acid was added with stirring at 30 to 35° C. over 10 minutes. Then, after stirring was continued at 20° C. for 20 minutes, the generated water and methanol were distilled under a reduced pressure at 50° C. After removal of sodium chloride by filtration, 125.7 g of distillate was obtained at 78 to 79° C. under a reduce pressure of 0.8 kPa (6 torr).

The results of nuclear magnetic resonance spectrometry were as follows: $^1$H-NMR (400 MHz, d6-DMSO, δ ppm), 4.425 (t, 2H, J=4.8 Hz), 4.329 (s, 2H), 3.832 (t, 2H, J=4.8 Hz), $^{13}$C-NMR (100 MHz, $d_6$-DMSO, δ ppm), 62.715, 66.430, 69.430, 167.782, confirming that it was 2-p-dioxanone.

The melting point was 24.2° C., the purity measured by gas chromatography was 99.1%, and the yield based on sodium monochloroacetate was 66.7%.

EXAMPLE 3

(Synthesis of 2-p-Dioxanone)

301.5 g (1.50 mol) of sodium β-hydroxyethoxy acetate obtained by the method of Example 1 was mixed with 500 ml of dioxane, to which 72.6 g (0.73 mol) of 98% sulfuric acid was dropped with stirring at 25 to 30° C. over 20 minutes. After that, stirring was continued at 20° C. for 20 minutes and then sodium chloride and sodium sulfate hydrate were removed by filtration to obtain 106.7 g of 2-p-dioxanone that was distilled at 78 to 79° C. under a reduced pressure of 0.8 kPa (6 torrs).

The melting point was 26.1° C., the purity measured by gas chromatography was 99.4%, and the yield based on sodium monochloroacetate was 56.8%.

EXAMPLE 4 AND 5

(Polymerization of 2-p-Dioxanone)

The water contents of the monomers obtained in Examples 2 and 3 measured were 34.4 and 25.7 ppm, respectively, which indicate sufficient quality for polymerization.

In a nitrogen box, each 10 g (0.098 mol) of the monomer, 0.022 g ($1.18 \times 10^{-4}$ mol) of lauryl alcohol, and a tin octanate ($3.92 \times 10^{-6}$ mol) solution in toluene were weighed and charged in a sufficiently dried ampoule. After a reduction in pressure at room temperature, the ampoule was sealed with melting and heated on an oil bath at 95° C. for 12 hours. After the polymerization reaction was continued on the oil bath at 80° C. for further 7 days, polymer was recovered. The solution viscosities (η) of the polymers thus obtained were measured using 0.1 g/dl of hexafluroroisopropanol at 25° C., which were 2.20 and 2.43, respectively.

Comparative Example 1

2-p-Dioxanone was manufactured according to the known manufacturing process described in Japanese Patent Publication No. 60-36785. The monomer thus obtained had a purity of 75.81% measured by gas chromatography. After the first distillation, the monomer contained ethylene glycol. Then the polymerization reaction was conducted by operation similar to that in Example 4. The solution viscosity (η) of the polymer was 0.12.

Figure 2:
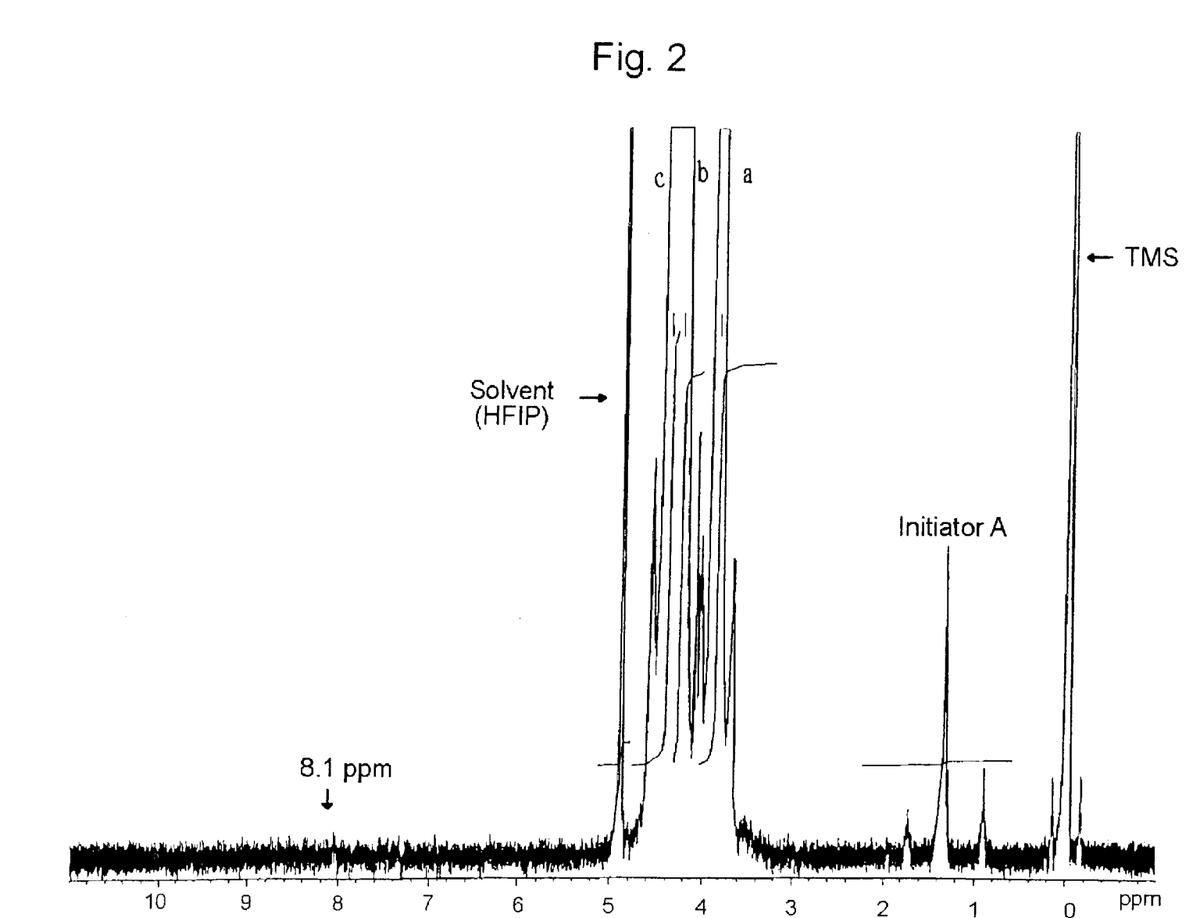
FIG. 2 is shown a nuclear magnetic resonance (NMR, measured at 25° C.) spectrum of the polyparadioxane with a high molecular weight and a narrow molecular weight distribution obtained by a polymerization reaction of the purified 2-p-dioxanone according to the present invention obtained in Example 3.

FIG. 2 is shown a nuclear magnetic resonance (NMR, measured at 25° C.) spectrum of the polyparadioxane with a high molecular weight and a narrow molecular weight distribution obtained by a polymerization reaction of the purified 2-p-dioxanone according to the present invention obtained in Example 3.

In the nuclear magnetic resonance (NMR, measured at 25° C.) spectrum of the polyparadioxane obtained by a polymerization reaction of the 2-p-dioxanone obtained in Comparative Example 1, a peak at 8.1 ppm attributable to a proton of a carboxyl group at a molecular end of the polymer was detected. However, as shown in FIG. 2, in the nuclear magnetic resonance (NMR, measured at 25° C.) spectrum of the polyparadioxane obtained by a polymerization reaction of the 2-p-dioxanone obtained in Example 3, a peak at 8.1 ppm attributable to a proton of a carboxyl group at a molecular end of the polymer was not detected.

It is therefore considered that while polyparadioxane obtained by a polymerization reaction of 2-p-dioxanone obtained in Comparative Example 1 had a low molecular weight and wide molecular weight distribution, a polyparadioxane obtained by a polymerization reaction of a purified 2-p-dioxanone according to the present invention obtained in Example 3 has a high molecular weight and narrow molecular weight distribution.

Thus, polymers having a high molecular weight and a narrow molecular weight distribution are extremely favorably used for biodegradable absorbable polymers used for drugs and the like and sutures for surgical operation and the like.

The abscissa axis shows ppm and the ordinate axis shows strength. In FIG. 2, symbols a, b, and c represent protons at positions a, b, and c shown together with arrows in the following formula (6), respectively.

The following formula (6) represents a repeating unit of polyparadioxane subjected to nuclear magnetic resonance spectrometry (NMR, measured at 25° C.).

(6)

In formula (6), R represents an alkyl group; symbols a, b, and c represent positions of protons in the repeating unit, and n represents a degree of polymerization.

What is claimed is:

1. A purified salt of β-hydroxyethoxy acetic acid which is characterized by detecting fusion peak-top temperature by differential scanning calorimetry (DSC) and which is represented by formula (1).

(1)

wherein in formula (1), n=1–2, and if n=1, M is Na and/or K, and, if n=2, M is Ca and/or Mg.

2. The purified salt of β-hydroxyethoxy acetic acid as claimed in claim 1, wherein the fusion peak-top temperature is 205 to 208° C.

3. The purified salt of β-hydroxyethoxy acetic acid as claimed in claim 1, wherein the fusion peak-top temperature is 206 to 207° C.

4. The purified salt of β-hydroxyethoxy acetic acid as claimed in claim 1, wherein the fusion peak-top temperature is 206.5° C.

5. A process of manufacturing a purified salt of β-hydroxyethoxy acetic acid represented by the following formula (1), of which a fusion peak-top temperature is detected by differential scanning calorimetry, characterized in that the process comprises the steps of:

sedimenting a salt of β-hydroxyethoxy acetic acid of formula (1), a fusion peak-top temperature of which is not detected by differential scanning calorimetry, with a poor solvent; and washing a sedimented salt of β-hydroxyethoxy acetic acid with the poor solvent, (1)

wherein in formula (1), n=1–2, and if n=1, M is Na and/or K, and, if n=2, M is Ca and/or Mg.

6. The process of manufacturing a purified salt of β-hydroxyethoxy acetic acid as claimed in claim 5, wherein the fusion peak-top temperature of an obtained purified salt of β-hydroxyethoxy acetic acid is 205 to 208° C.

7. The process of manufacturing a purified salt of β-hydroxyethoxy acetic acid as claimed in claim 5, wherein the fusion peak-top temperature of an obtained purified salt of β-hydroxyethoxy acetic acid is 206 to 207° C.

8. The process of manufacturing a purified salt of β-hydroxyethoxy acetic acid according as claimed in claim 5, wherein the fusion peak-top temperature of an obtained purified salt of β-hydroxyethoxy acetic acid is 206.5° C.

9. A purified salt of β-hydroxyethoxy acetic acid represented by the following formula (1) obtained by the process according to the manufacturing method as claimed in claim 8, (1)

wherein in formula (1), n=1–2, and if n=1, M is Na and/or K, and, if n=2, M is Ca and/or Mg.

10. A process of manufacturing a purified 2-p-dioxanone represented by the following formula (2), characterized in that a purified salt of β-hydroxyethoxy acetic acid represented by the following formula (1), a fusion peak-top temperature of which is detected by differential scanning calorimetry, is reacted with an inorganic acid, whereby a neutralization reaction and a cyclization reaction are performed in the same system, (1)

wherein in formula (1), n=1–2, and if n=1, M is Na and/or K, and, if n=2, M is Ca and/or Mg (2)

11. The process of manufacturing a purified 2-p-dioxanone as claimed in claim 10, wherein the fusion peak-top temperature of the purified salt of β-hydroxyethoxy acetic acid employed is 205 to 208° C.

12. The process of manufacturing a purified 2-p-dioxanone as claimed in claim 10, wherein the fusion peak-top temperature of the purified salt of β-hydroxyethoxy acetic acid employed is 206 to 207° C.

13. The process of manufacturing a purified 2-p-dioxanone as claimed in claim 10, wherein the fusion peak-top temperature of the purified salt of β-hydroxyethoxy acetic acid employed is 206.5° C.

14. A purified 2-p-dioxanone obtained by the manufacturing process described in claim 13.

15. The purified 2-p-dioxanone as claimed in claim 14, wherein the purified 2-p-dioxanone has a function to produce a polyparadioxane not having a carboxyl group at molecular ends after a polymerization reaction.

16. The purified 2-p-dioxanone as claimed in claim 14, wherein the purified 2-p-dioxanone has a function to produce a polyparadioxane for which a peak at 8.1 ppm attributable to a proton of a carboxyl group by nuclear magnetic resonance spectrometry is not detected after a polymerization reaction.

17. A purified salt of β-hydroxyethoxy acetic acid represented by the following formula (1) obtained by the process according the manufacturing method as claimed in claim 7, (1)

wherein in formula (1), n=1–2, and if n=1, M is Na and/or K, and, if n=2, M is Ca and/or Mg.

18. A purified salt of β-hydroxyethoxy acetic acid represented by the following formula (1) obtained by the process according to any one of the manufacturing methods as claimed in claim 6, (1 wherein in formula (1), n=1–2, and if n=1, M is Na and/or K, and, if n=2, M is Ca and/or Mg.

19. A purified salt of β-hydroxyethoxy acetic acid represented by the following formula (1) obtained by the process according to the manufacturing method as claimed in claim 5, (1)

wherein in formula (1), n=1–2, and if n=1, M is Na and/or K, and, if n=2, M is Ca and/or Mg.

20. A purified 2-p-dioxanone obtained by the manufacturing process described in claim 12.

21. The purified 2-p-dioxanone as claimed in claim 20, wherein the purified 2-p-dioxanone has a function to produce a polyparadioxane not having a carboxyl group at molecular ends after a polymerization reaction.

22. The purified 2-p-dioxanone as claimed in claim 20, wherein the purified 2-p-dioxanone has a function to produce a polyparadioxane for which a peak at 8.1 ppm attributable to a proton of a carboxyl group by nuclear magnetic resonance spectrometry is not detected after a polymerization reaction.

23. A purified 2-p-dioxanone obtained by the manufacturing process described in claim 11.

24. The purified 2-p-dioxanone as claimed in claim 23, wherein the purified 2-p-dioxanone has a function to produce a polyparadioxane not having a carboxyl group at molecular ends after a polymerization reaction.

25. The purified 2-p-dioxanone as claimed in claim 23, wherein the purified 2-p-dioxanone has a function to produce a polyparadioxane for which a peak at 8.1 ppm attributable to a proton of a carboxyl group by nuclear magnetic resonance spectrometry is not detected after a polymerization reaction.

26. A purified 2-p-dioxanone obtained by the manufacturing process described in claim 10.

27. The purified 2-p-dioxanone as claimed in claim 26, wherein the purified 2-p-dioxanone has a function to produce a polyparadioxane not having a carboxyl group at molecular ends after a polymerization reaction.

28. The purified 2-p-dioxanone as claimed in claim 26, wherein the purified 2-p-dioxanone has a function to produce a polyparadioxane for which a peak at 8.1 ppm attributable to a proton of a carboxyl group by nuclear magnetic resonance spectrometry is not detected after a polymerization reaction.

* * * * *

UNITED STATES PATENT AND TRADEMARK OFFICE
CERTIFICATE OF CORRECTION

PATENT NO.    : 6,384,241 B2
DATED         : May 7, 2002
INVENTOR(S)   : Satoru Nakatani et al.

It is certified that error appears in the above-identified patent and that said Letters Patent is hereby corrected as shown below:

<u>Title page,</u>
Item [30], Foreign Application Priority Data, change:
"Mar. 21, 2001   (JP)      2001-079955" to
-- Mar. 31, 2001   (JP)      2000-098225 --

Signed and Sealed this

Twenty-seventh Day of May, 2003

JAMES E. ROGAN
*Director of the United States Patent and Trademark Office*